(12) United States Patent
Kalyankar et al.

(10) Patent No.: US 8,252,336 B2
(45) Date of Patent: Aug. 28, 2012

(54) ESCITALOPRAM AND SOLID PHARMACEUTICAL COMPOSITION COMPRISING THE SAME

(75) Inventors: Parshwakumar V. Kalyankar, Goa (IN); Ganesh V. Gat, Goa (IN); Jawed Hussain, Goa (IN)

(73) Assignee: Ratiopharm GmbH, Ulm (DE)

( * ) Notice: Subject to any disclaimer, the term of this patent is extended or adjusted under 35 U.S.C. 154(b) by 436 days.

(21) Appl. No.: 12/446,246

(22) PCT Filed: Oct. 18, 2007

(86) PCT No.: PCT/EP2007/009040
§ 371 (c)(1),
(2), (4) Date: Apr. 28, 2009

(87) PCT Pub. No.: WO2008/046617
PCT Pub. Date: Apr. 24, 2008

(65) Prior Publication Data
US 2010/0323017 A1    Dec. 23, 2010

(30) Foreign Application Priority Data
Oct. 20, 2006   (IN) .......................... 1931/CHE/2006

(51) Int. Cl.
*A61K 9/26* (2006.01)
*A61K 31/343* (2006.01)
*C07D 307/78* (2006.01)

(52) U.S. Cl. .................. 424/489; 514/469; 549/467
(58) Field of Classification Search .................. 424/489; 514/469; 549/467
See application file for complete search history.

(56) References Cited

U.S. PATENT DOCUMENTS

| 4,943,590 A * | 7/1990 | Boegesoe et al. ............. 514/469 |
| 2005/0147674 A1 | 7/2005 | Christensen et al. |

FOREIGN PATENT DOCUMENTS

| EP | 1152000 A1 | 11/2001 |
| WO | WO 03/011278 | 2/2003 |
| WO | WO 2005/084643 | 9/2005 |
| WO | WO 2006/123243 | 11/2006 |
| WO | WO 2007/053904 | 5/2007 |
| WO | WO 2007053904 A1 * | 5/2007 |

OTHER PUBLICATIONS

Vippagunta, S., Crystalline Solids, 2001, Advanced Drug Delivery Reviews, vol. 48, pp. 3-26.*
Braga, D., Making Crystals from Crystals: A Green Route to Crystal Engineering and Polymorphism, 2005, Chem. Commun, pp. 3635-3645.*
Seddon, K., Pseudopolymorph: A Polemic, 2004, Crystal Growth and Design, vol. 4, Issue 6, pp. 1087-1088.*

* cited by examiner

*Primary Examiner* — John Pak
*Assistant Examiner* — Andriae M Holt
(74) *Attorney, Agent, or Firm* — Chalin A. Smith; Smith Patent Consulting, LLC

(57) ABSTRACT

The present invention relates to Escitalopram having a small median particle size and a solid pharmaceutical composition comprising the same.

7 Claims, 1 Drawing Sheet

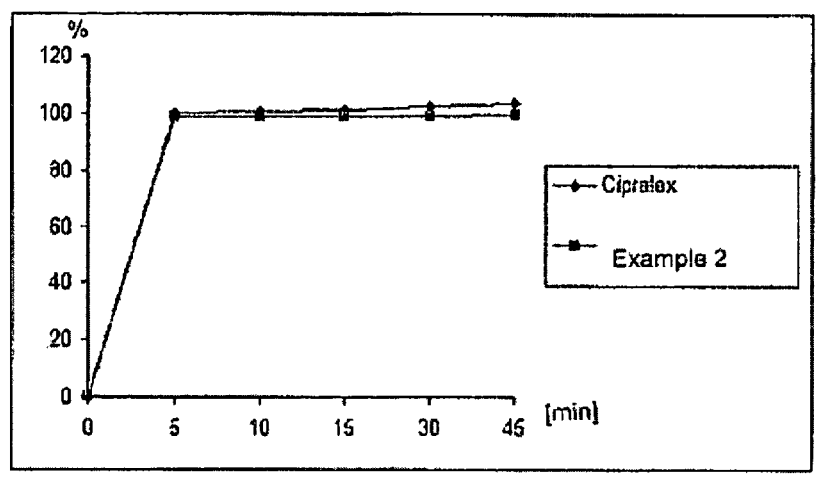

ESCITALOPRAM AND SOLID PHARMACEUTICAL COMPOSITION COMPRISING THE SAME

This application corresponds to the national phase of International Application No. PCT/EP07/009040, filed Oct. 18, 2007, which, in turn, claims priority to Indian Patent Application No. 1931/CHE/2006, filed Oct. 20, 2006, the contents of both of which are incorporated by reference herein in their entirety.

The present invention relates to Escitalopram having a small median particle size and a solid pharmaceutical composition comprising the same.

Escitalopram is the S-enantiomer of the antidepressant drug Citalopram, i.e. (S)-1-[3-(dimethylamino)propyl]-1-(4-fluorophenyl)-1,3-dihydro-5-isobenzofurancarbonitrile. Citalopram has the following chemical structure:

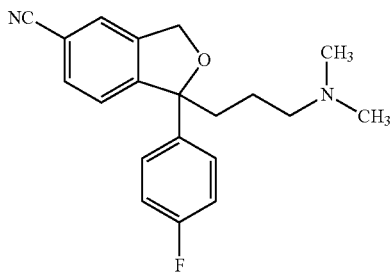

Citalopram was first disclosed in DE 2 657 013 which also discloses methods for preparing this compound. The Citalopram prepared was isolated in crystalline form as the oxalate, the hydrobromide and the hydrochloride salt, respectively. Citalopram is marketed as the hydrobromide.

Escitalopram, the pharmaceutical activity thereof and crystalline escitalopram oxalate are disclosed in U.S. Pat. No. 4,943,590. Methods for preparation of pharmaceutical preparations of Escitalopram are also outlined.

Citalopram is marketed in a number of countries as a tablet prepared by either direct compression or compression of granulated citalopram hydrobromide, lactose and other excipients.

It is well recognized that the preparation of tablets with a reproducible composition requires that all the dry ingredients have good flow properties. In cases, where the active ingredient has good flow properties, tablets can be prepared by direct compression of the ingredients. However, in many cases the particle size of the active substance is small, the active substance is cohesive or has poor flow properties. Furthermore, active substances with a small particle size mixed with excipients having a larger particle size will typically segregate or de-mix during the tabletting process. The problem of small particle size and poor flowability is conventionally solved by enlarging the particle size of the active substance, usually by granulation of the active ingredient either alone or in combination with a filler and/or other conventional tablet ingredients. However, also granulation of the active ingredient may be difficult if the flow behaviour is poor. Moreover, additional time and energy consuming and, thus, costly preparation steps are required.

WO 2003/011278 aims at avoiding such problems by providing larger crystals of Escitalopram oxalate having a median particle size of at least 40 μm via a novel crystallization process.

WO 2005/084643 discloses that crystalline particles of Escitalopram oxalate though having a smaller particle size as those disclosed in WO 2003/011278 are nevertheless suitable for use in direct compression if they have a wide particle size distribution being defined in that the ratio between the median particle size and the particle size at 95% quantile is less than 0.42. Nevertheless, the median particle size of the Escitalopram oxalate crystalline particles should be at least 20 μm.

Preparing Escitalopram particles having a relatively large particle size according to the method of WO 2003/011278 or a large particle size distribution according to WO 2005/084643 requires additional steps and efforts in the preparation method which therefore becomes more costly. Therefore, there is still a need for Escitalopram which can easily be manufactured into solid pharmaceutical compositions and which can be obtained in an easy and cost efficient manner.

It has now surprisingly been found that Escitalopram having a small median particle size can nevertheless be easily formulated into solid pharmaceutical compositions if it has a narrow particle size distribution. Therefore, the present invention relates to Escitalopram or pharmaceutically acceptable salt and/or solvate thereof being in the form of particles having a median particle size of less than 40 μm, characterized in that the ratio between the median particle size and the particle size at the 95% quantile is equal to or greater than 0.42.

Surprisingly it has been found that contrary to the disclosure of WO 2003/011278 and WO 2005/084643 and the general knowledge of the person skilled in the art Escitalopram having a small particle size does not show the expected disadvantages in flow behaviour and, thus, processability if it is provided as particles having a narrow particle size distribution. In this case the active ingredient can be easily handled, mixed with excipients even having a larger particle size and can be processed into pharmaceutical compositions such as tablets or capsules without the known and expected problems such as segregation or de-mix during the processing steps. It is even possible to prepare tablets by direct compression without the requirement or previous granulation of the active ingredient into larger particles in order to increase the flow properties. Likewise the granulation is possible as well, because the flow behaviour of the Escitalopram of a small medium particle size and a narrow particle size distribution facilitates the granulation process. Thus, it is possible to prepare pharmaceutical compositions with the Escitalopram of the present invention in a fast and cost efficient manner. It has also surprisingly been found that with Escitalopram being in the form of small particles and having the particle size distribution of the present invention accurate dosing of the active ingredient and excipients into capsules is possible without the expected problems, such as de-mix of the ingredients during processing.

Due to its good flow properties Escitalopram of the present invention is suitable for the preparation of tablets by direct compression. In particular, it is not necessary to first prepare granules of the active ingredient with other excipients before compression of these granules into tablets.

BRIEF DESCRIPTION OF THE DRAWING

FIG. 1 shows the dissolution profile of the commercially available Cipralex® tablets and Example 2.

As used herein "direct compression" means that the solid unit dosage form is prepared by compression of a simple mixture of the active ingredient and excipients, without the active ingredient having been subjected to an intermediate granulation process in order to imbed it in a larger particle and improve its fluidity properties.

Alternatively, the Escitalopram of the present invention can be used to prepare a premix with suitable excipients. This premix can then be used in a granulation process or for filling capsules.

As used herein, "particle size distribution" means the cumulative volume size distribution of equivalent spherical diameters as determined by laser diffraction at 1 bar dispersive pressure in a Sympatec Helos equipment. "Median particle size", correspondingly, means the median of said particle size distribution. When the term "Escitalopram" is used it covers Escitalopram as well as a pharmaceutically acceptable salt and/or a pharmaceutically acceptable solvate thereof.

Thus, in a first aspect the present invention relates to Escitalopram or a pharmaceutically acceptable salt and/or solvate thereof having a median particle size of less than 40 µm and wherein the ratio between the median particle size and the particle size at the 95% quantile is equal to or greater than 0.42. The Escitalopram may be in amorphous or crystalline form, preferably it is in the form of crystalline particles. Preferably the median particle size is less than 20 µm, more preferably less than 10 µm, and most preferably between 4 µm and 8 µm.

In order to achieve the unexpected good results of the present invention the Escitalopram must have a narrow particle size distribution being defined by the ratio between the median particle size and the particle size at the 95% quantile. This ratio must be equal to or greater than 0.42, preferably greater than 0.45, more preferably greater than 0.50 and most preferably between 0.55 and 0.70, such as for example about 0.60±0.02.

The Escitalopram preferably is present in the form of a pharmaceutically acceptable salt thereof. As pharmaceutically acceptable salts the hydrobromide, hydrochloride, and oxalate can be mentioned. The oxalate salt of Escitalopram is preferred. The Escitalopram of the present invention is particularly suitable for the preparation of solid pharmaceutical compositions. Therefore, in a further embodiment the present invention relates to a solid pharmaceutical composition comprising Escitalopram or a pharmaceutically acceptable salt and/or solvate thereof wherein the Escitalopram is in the form of particles having a median particle size of less than 40 µm, characterized in that the ratio between the median particle size and the particle size at the 95% quantile is equal to or greater than 0.42.

Preferably, the solid pharmaceutical composition is in the form of a tablet or capsule. The process for preparing the pharmaceutical composition may comprise the step of direct compression, wet granulation and/or dry compaction.

The solid pharmaceutical composition according to the invention may contain 1-60% by weight active ingredient calculated as Escitalopram base, preferably 4-40% by weight active ingredient calculated as Escitalopram base. For example, the solid pharmaceutical composition in the form of a unit dosage form may comprise 5 mg, 10 mg, 15 mg or 20 mg Escitalopram base.

The solid pharmaceutical composition of the present invention may further comprise excipients, such as diluents, binders, disintegrants, glidants, lubricants, levigating agents and/or film coating agents. As diluents and binders mannitol, lactose, starch and microcrystalline cellulose can be exemplified. As disintegrants L-hydroxypropyl cellulose and cross-carmellose can be exemplified. As glidants talc and colloidal anhydrous silica can be exemplified. As lubricants talc and magnesium stearate can be exemplified. As levigating agent glycerin can be exemplified. As film coating agents methylhydroxypropylcellulose and Eudragit® can be exemplified.

Besides the above compounds the pharmaceutical composition of the present invention may comprise various other conventional excipients as known to the person skilled in the art. Optionally minor amounts of colorants and sweeteners may also be present.

Optionally, the solid pharmaceutical composition of the present invention may be coated. Suitably the coating is a film coating based on conventional coating mixtures such as Opadry white 03B28796, manufactured by Colorcon.

The solid pharmaceutical composition of the present invention may be prepared by conventional methods as known to those skilled in the art. The tablets may be prepared by conventional tabletting methods. The tablets can be prepared by direct compression without an intermediate granulation step. Alternatively, the tablets can be prepared by granulating a premix comprising the Escitalopram of the present invention and one or more excipients, and forming the thus obtained granules into tablets. In a further embodiment the premix comprising the active ingredient together with one or more excipients may be filled into capsules, such as hard gelatine capsules by conventional methods, for example using a capsule filler suitable for powder filling. The premix preferably is in the form of a powder, in particular a dry powder.

Surprisingly, tablets prepared with Escitalopram oxalate of the present invention nevertheless exhibit a dissolution profile being very similar to the dissolution profile of the commercially available Cipralex® tablets. Preferably the pharmaceutical composition of the present invention is a bio equivalent solid dosage form for Cipralex®.

In a further aspect the present invention relates to the use of Escitalopram or a pharmaceutically acceptable salt and/or solvate thereof as described above for the preparation of solid pharmaceutical compositions.

The following examples are merely intended to illustrate the invention and should not be construed as limiting.

In the following examples Escitalopram oxalate having a median particle size between of about 6.65 µm and a ratio between the median particle size and the particle size at the 95% quantile of about 0.61 is employed.

EXAMPLE 1

| Item No. | Ingredients | Percentage (%) | Function |
|---|---|---|---|
| 1. | Escitalopram oxalate | 9.83% | Active Pharmaceutical Ingredient |
| 2. | Pearlitol 200 SD | 31.70% | Diluent |
| 3. | Microcrystalline cellulose102 | 47.50% | Diluent |
| 4. | L-Hydroxy propyl cellulose LH21 | 3.00% | Disintegrant |
| 5. | Colloidal silicon dioxide | 0.50% | Glidant |
| 6. | Talc | 5.00% | Glidant/lubricant |
| Lubrication | | | |
| 7. | Magnesium stearate | 1.00% | Lubricant |
| Film coating | | | |
| 8. | Opadry white 03B28796 | 1.50% | Film Coating agent |
| 9. | Purified water | q.s. | Solvent |
| | Total Weight (260.0 mg for 20 mg strength) | 100.0% | |

Process:
   I. Weigh accurately all the above ingredients as per respective quantity.
   II. Mix item no. 2, 3, 4, and 5 and sift through #40 mesh.
   III. Mix item no. 1 and item no. 6 and sift through #40 mesh.
   IV. Mix step II with step III continue blending for adequate time period and sift through #40 mesh.
   V. Sift item no. 7 through #40 mesh.
   VI. Lubricate the blend of step IV with sifted item of step V.
   VII. Compress the blend of step VI as per specified parameters*.
   VIII. Film coat the step VII core tablets with use of an appropriate coating pan/machine with up to standard parameters.

*Compression Parameters:
Avg. wt. of core tablet: 256 mg±2%, Hardness: NLT 80 N
Avg. wt. of film coated tablet: 260 mg±2%.

This example involves direct compression, however is also suitable for wet granulation and for dry compaction.

EXAMPLE 2

| Item No. | Ingredients | Percentage (%) | Function |
| --- | --- | --- | --- |
| 1. | Escitalopram oxalate | 9.83% | Active Pharmaceutical Ingredient |
| 2. | Pharmatose DCL21 | 29.19% | Diluent |
| 3. | Microcrystalline cellulose 102 | 50.00% | Diluent |
| 4. | L-Hydroxy propyl cellulose LH21 | 3.00% | Disintegrant |
| 5. | Colloidal silicon dioxide | 0.50% | Glidant |
| 6. | Talc | 5.00% | Glidant/lubricant |
| Lubrication | | | |
| 7. | Magnesium stearate | 1.00% | Lubricant |
| Film coating | | | |
| 8. | Opadry white 03B28796 | 1.50% | Film Coating agent |
| 9. | Purified water | q.s. | Solvent |
| | Total Weight (260.0 mg for 20 mg strength) | 100.0% | |

Process:
   I. Weigh accurately all the above ingredients as per respective quantity.
   II. Mix item no. 2, 3, 4, and 5 and sift through #40 mesh.
   III. Mix item no. 1 and item no. 6 and sift through #40 mesh.
   IV. Mix step II with step III continue blending for adequate time period and sift through #40 mesh.
   V. Sift item no. 7 through #40 mesh.
   VI. Lubricate the blend of step IV with sifted item of step V.
   VII. Compress the blend of step VI as per specified parameters*.
   VIII. Film coat the step VII core tablets with use of an appropriate coating pan/machine with up to standard parameters.

*Compression Parameters:
Avg. wt. of core tablet: 256 mg±2%, Hardness: NLT 80 N
Avg. wt. of film coated tablet: 260 mg±2%.

This example involves direct compression, however is also suitable for wet granulation and for dry compaction.

EXAMPLE 3

| Item No. | Ingredients | Percentage (%) | Function |
| --- | --- | --- | --- |
| Process (Direct Compression) | | | |
| 1. | Escitalopram oxalate | 9.83% | Active Pharmaceutical Ingredient |
| 2. | Starch 1500 | 15.84% | Diluent/Binder |
| 3. | Microcrystalline cellulose102 | 63.35% | Diluent |
| 4. | L-Hydroxy propyl cellulose LH21 | 3.00% | Disintegrant |
| 5. | Colloidal silicon dioxide | 0.50% | Glidant |
| 6. | Talc | 5.00% | Glidant/lubricant |
| Lubrication | | | |
| 7. | Magnesium stearate | 1.00% | Lubricant |
| Film coating | | | |
| 8. | Opadry white 03B28796 | 1.5% | Film Coating agent |
| 9. | Purified water | q.s. | Solvent |
| | Total Weight (260.0 mg for 20 mg strength) | 100% | |

Process:
   I. Weigh accurately all the above ingredients as per respective quantity.
   II. Mix item no. 2, 3, 4, and 5 and sift through #40 mesh.
   III. Mix item no. 1 and item no. 6 and sift through #40 mesh.
   IV. Mix step II with step III continue blending for adequate time period and sift through #40 mesh.
   V. Sift item no. 7 through #40 mesh.
   VI. Lubricate the blend of step IV with sifted item of step V.
   VII. Compress the blend of step VI as per specified parameters*.
   VIII. Film coat the step VII core tablets with use of an appropriate coating pan/machine with up to standard parameters.

*Compression Parameters:
Avg. wt. of core tablet: 256 mg±2%, Hardness: NLT 80 N
Avg. wt. of film coated tablet: 260 mg±2%.

This example involves direct compression, however is also suitable for wet granulation and for dry compaction.

EXAMPLE 4

| Item No. | Ingredients | Percentage (%) | Function |
| --- | --- | --- | --- |
| Process (Direct Compression) | | | |
| 1. | Escitalopram oxalate | 9.83% | Active Pharmaceutical Ingredient |
| 2. | Starch 1500 | 15.84% | Diluent/Binder |
| 3. | Pearlitol 200 SD | 63.35% | Diluent |
| 4. | L-Hydroxy propyl cellulose LH21 | 3.00% | Disintegrant |
| 5. | Colloidal silicon dioxide | 0.50% | Glidant |
| 6. | Talc | 5.00% | Glidant/lubricant |

-continued

| Item No. | Ingredients | Percentage (%) | Function |
|---|---|---|---|
| | Lubrication | | |
| 7. | Magnesium stearate | 1.00% | Lubricant |
| | Film coating | | |
| 8. | Opadry white 03B28796 | 1.50% | Film Coating agent |
| 9. | Purified water | q.s. | Solvent |
| | Total Weight (260.0 mg for 20 mg strength) | 100.0% | |

Process:
I. Weigh accurately all the above ingredients as per respective quantity.
II. Mix item no. 2, 3, 4, and 5 and sift through #40 mesh.
III. Mix item no. 1 and item no. 6 and sift through #40 mesh.
IV. Mix step II with step III continue blending for adequate time period and sift through #40 mesh.
V. Sift item no. 7 through #40 mesh.
VI. Lubricate the blend of step IV with sifted item of step V.
VII. Compress the blend of step VI as per specified parameters*.
VIII. Film coat the step VII core tablets with use of an appropriate coating pan/machine with up to standard parameters.

*Compression Parameters:
Avg. wt. of core tablet: 256 mg±2%, Hardness: NLT 80 N
Avg. wt. of film coated tablet: 260 mg±2%.

This example involves direct compression, however is also suitable for wet granulation and for dry compaction.

EXAMPLE 5

| Item No. | Ingredients | Percentage (%) | Function |
|---|---|---|---|
| | Process (Direct Compression) | | |
| 1. | Escitalopram oxalate | 9.83% | Active Pharmaceutical Ingredient |
| 2. | Starch 1500 | 15.00% | Diluent/Binder |
| 3. | Pearlitol 200 SD | 63.19% | Diluent |
| 4. | Glycerin | 1.00% | Levigating agent |
| 5. | L-Hydroxy propyl cellulose LH21 | 3.00% | Disintegrant |
| 6. | Colloidal silicon dioxide | 0.50% | Glidant |
| 7. | Talc | 5.00% | Glidant/lubricant |
| | Lubrication | | |
| 8. | Magnesium stearate | 1.00% | Lubricant |
| | Film coating | | |
| 9. | Opadry white 03B28796 | 1.50% | Film Coating agent |
| 10. | Purified water | q.s. | Solvent |
| | Total Weight (260.0 mg for 20 mg strength) | 100.0% | |

Process:
I. Weigh accurately all the above ingredients as per respective quantity.
II. Mix item no. 2, 3, 5, and 6 and sift through #40 mesh.
III. Levigate item no. 1 by item no. 4
IV. Mix step III and item no. 6 and sift through #40 mesh.
V. Mix blend of step II with blend of step III continue blending for adequate time period and sift through #40 mesh.
VI. Sift item no. 7 through #40 mesh.
VII. Lubricate the blend of step IV with sifted item of step V.
VIII. Compress the blend of step VI as per specified parameters*.
IX. Film coat the step VII core tablets with use of an appropriate coating pan/machine with up to standard parameters.

*Compression Parameters:
Avg. wt. of core tablet: 256 mg±2%, Hardness: NLT 80 N
Avg. wt. of film coated tablet: 260 mg±2%.

This example involves direct compression, however is also suitable for wet granulation and for dry compaction.

EXAMPLE 6

| Item No. | Ingredients | Percentage (%) | Function |
|---|---|---|---|
| 1. | Escitalopram oxalate | 9.83% | Active Pharmaceutical Ingredient |
| 2. | Microcrystalline cellulose PH 101 | 40.00% | Diluent |
| 3. | Lactose Monohydrate | 25.79% | Diluent |
| 4. | Crosscarmellose sodium | 2.70% | Disintegrant |
| 5. | Maize starch | 5.00% | Binder |
| 6. | Glycerol | 0.35% | Co-solvent |
| 7. | Purified water | q.s. | Solvent |
| | Extra-granular | | |
| 8. | Copovidone | 2.61% | Binder |
| 9. | Crosscarmellose sodium | 2.00% | Disintegrant |
| 10. | Maize starch | 0.96% | Disintegrant |
| 11. | Microcrystalline cellulose PH 101 | 7.76% | Anti-adherent/ disintegrant |
| | Lubrication | | |
| 12. | Magnesium stearate | 1.00% | Lubricant |
| | Film coating | | |
| 13. | Opadry white 03B28796 | 2.00% | Film Coating agent |
| 14. | Purified water | q.s. | Solvent |
| | Total Weight (260.0 mg for 20 mg strength) | 100.0% | |

Process:
I. Weigh accurately all the above ingredients as per respective quantity.
II. Mix item no. 1, 2, 3 and 4 and sift through #40 mesh.
III. Prepare paste with item no. 7, 6, and 5
IV. Granulate step II in an appropriate granulator.
V. Dry step V as to get up to standard loss of drying (%) and sift through #30 mesh.
VI. Mix item no. 8, 9, 10 and 11 and sift though #30 mesh.
VII. Mix step VI with step V.
VIII. Sift item no. 12 through #40 mesh.
IX. Lubricate the blend of step VII with sifted item of step VIII.
X. Compress the blend of step IX as per specified parameters*.
XI. Film coat the step X core tablets with use of an appropriate coating pan/machine with up to standard parameters.

*Compression Parameters:
Avg. wt. of core tablet: 256 mg±2%, Hardness: NLT 80 N
Avg. wt. of film coated tablet: 260 mg±2%.

EXAMPLE 7

| Item No. | Ingredients | Percentage (%) | Function |
|---|---|---|---|
| | Process (Direct Compression) | | |
| 1. | Escitalopram oxalate | 9.83% | Active Pharmaceutical Ingredient |
| 2. | Prosolv SMCC HD 90 | 79.07% | Diluent/Binder |
| 3. | Crosscarmellose sodium | 3.60% | Diluent |
| 4. | Talc | 5.00% | Glidant/lubricant |
| | Lubrication | | |
| 5. | Magnesium stearate | 1.00% | Lubricant |
| | Film coating | | |
| 6. | Opadry white 03B28796 | 1.50% | Film Coating agent |
| 7. | Purified water | q.s. | Solvent |
| | Total Weight (260.0 mg for 20 mg strength) | 100.0% | |

Process:
 I. Weigh accurately all the above ingredients as per respective quantity.
 II. Mix item no. 2 and 3 and sift through #40 mesh.
 III. Mix item no. 1 and item no. 4 and sift through #40 mesh.
 IV. Mix step II with step III continue blending for adequate time period and sift through #40 mesh.
 V. Sift item no. 5 through #40 mesh.
 VI. Lubricate the blend of step IV with sifted item of step V.
 VII. Compress the blend of step VI as per specified parameters*.
 VIII. Film coat the step VII core tablets with use of an appropriate coating pan/machine with up to standard parameters.

*Compression Parameters:
Avg. wt. of core tablet: 256 mg±2%, Hardness: NLT 80 N
Avg. wt. of film coated tablet: 260 mg±2%.

This example involves direct compression, however is also suitable for wet granulation and for dry compaction.

EXAMPLE 8

In this example the dissolution profiles of the tablets obtained by above Example 2 and the commercially available Cipralex® tablets are measured. The dissolution rates were measured in 900 ml of 0.1 M HCl using an USP Type II apparatus at 75 rpm. The results are summarized in the following table 1.

TABLE 1

| Time [min] | dissolution rate [%] Cipralex ® | dissolution rate [%] Example 2 |
|---|---|---|
| 0 | 0 | 0 |
| 5 | 99.72 | 98.54 |
| 10 | 100.32 | 98.72 |
| 15 | 101.24 | 98.73 |
| 30 | 102.23 | 99.04 |
| 45 | 103.15 | 99.05 |

The results are also shown in enclosed FIG. 1.

The above example demonstrates that the tablets prepared according to the present invention have a dissolution profile being very similar to the dissolution profile of the commercially available Cipralex® tablets.

The invention claimed is:

1. A solid pharmaceutical composition comprising Escitalopram or a pharmaceutically acceptable salt thereof in the form of particles having a median particle size of less than 10 µm, characterized in that the ratio between the median particle size and the particle size at the 95% quantile is between 0.55 and 0.70.

2. The solid pharmaceutical composition according to claim 1 being in the form of a tablet or capsule.

3. The solid pharmaceutical composition according to claim 2 being in the form of a tablet obtained by direct compression.

4. The solid pharmaceutical composition according to claim 2 being in the form of a tablet obtained by a process comprising a step of wet granulation or dry compaction.

5. A premix for preparing a pharmaceutical composition, wherein said premix comprises Escitalopram or a pharmaceutically acceptable salt thereof in the form of particles having a median particle size of less than 10 µm, characterized in that the ratio between the median particle size and the particle size at the 95% quantile is between 0.55 and 0.70, in combination with one or more excipients.

6. The solid pharmaceutical composition according to claim 1, wherein the particles have a median particle size between 4 µm and 8 µm.

7. The solid pharmaceutical composition according to claim 1, wherein the Escitalopram is in the form of an oxalate salt.

* * * * *